(12) United States Patent
Calias et al.

(10) Patent No.: US 6,610,669 B1
(45) Date of Patent: Aug. 26, 2003

(54) WATER INSOLUBLE DERIVATIVES OF POLYANIONIC POLYSACCHARIDES

(75) Inventors: Pericles Calias, Melrose; Robert J. Miller, Halifax, both of MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 09/469,638

(22) Filed: Dec. 22, 1999

(51) Int. Cl.$^7$ .................. A61K 31/715; C08B 37/00
(52) U.S. Cl. ............... 514/57; 514/54; 536/84; 536/88; 536/89; 536/98; 536/124
(58) Field of Search ............... 536/84, 88, 89, 536/98, 124; 514/54, 57

(56) References Cited

U.S. PATENT DOCUMENTS

| | | | |
|---|---|---|---|
| 3,998,974 A | | 12/1976 | Zaffaroni |
| 4,343,736 A | | 8/1982 | Uemura et al. |
| 4,526,716 A | | 7/1985 | Stevens |
| 4,582,865 A | | 4/1986 | Balazs et al. |
| 4,713,448 A | | 12/1987 | Balazs et al. |
| 4,774,093 A | | 9/1988 | Provonchee et al. |
| 4,810,784 A | | 3/1989 | Larm |
| 4,937,270 A | * | 6/1990 | Hamilton et al. ............ 514/777 |
| 4,970,298 A | | 11/1990 | Silver et al. |
| 4,973,493 A | | 11/1990 | Guire |
| 5,017,229 A | * | 5/1991 | Burns et al. ............ 106/162 |
| 5,128,326 A | | 7/1992 | Balazs et al. |
| 6,030,958 A | * | 2/2000 | Burns et al. ............ 514/57 |

FOREIGN PATENT DOCUMENTS

| | | |
|---|---|---|
| CA | 2022091 | 2/1991 |
| EP | 0 010 519 | 4/1980 |
| EP | 0193 510 | 9/1986 |
| EP | 0 224 987 | 6/1987 |
| EP | 0 224 178 | 11/1987 |
| EP | 0 291 177 | 11/1988 |
| EP | 0416 250 | 3/1991 |
| EP | 0 705 878 A2 | 4/1996 |
| EP | 0 705 878 A3 | 10/1996 |
| GB | 2 151 244 | 7/1985 |
| JP | 7102002 | 9/1993 |
| WO | WO 86/00079 | 1/1986 |
| WO | WO 86/00912 | 2/1986 |
| WO | WO86/04355 | 7/1986 |
| WO | WO 94/01468 | 1/1994 |
| WO | WO94/02517 | 2/1994 |
| WO | WO 94/21299 | 9/1994 |
| WO | WO 96/37519 | 11/1996 |

OTHER PUBLICATIONS

The Merck Index, 11th Edition, published by Merck & Co., Inc. (NJ), (1989), p. 9, cit, #47.*
Herman et al., "Heparin–modified polylactide as biodegradable hemcompatible biomaterial", *J. of Mater. Sci., Materials in Medicine*, 5:9, pp. 728–731 (1994).
Sparer et al., Controlled Release from Glycosaminoglycan Drug Complexes, *Controlled Release Delivery Systems*, Chapter 6, pp. 107–119 (1983).
Danishefsky et al., "Conversion of Carboxyl Groups of Mucopolysaccharides into Amides of Amino Acid Esters", *Carbohydrate Research*, 16, pp. 199–205 (1971).
Laurent et al., "Cross–linked Gels of Hyaluronic Acid", *Acta Chemica Scandinava*, 18:274–275 (1964).
Goodman & Gilman's the Pharmacological Basis of Therapeutics, Gilman et al., eds., Pergamon Press, NY, p. 1313 (1990).
Pouyani et al., The Pharmacological Basis of Therapeutics, Gilman et al., eds., Pergamon Press, NY, p. 1313 (1990).
Kuo et al., Chemical Modification of hyaluronic Acid by Carbodiimides, Bioconjugate Chem., 2, pp. 232–241 (1990).
Staros, J. V., "Membrane–Impermeant Cross–Linking Reagents: Probes of the Structure and Dynamics of Membrane Proteins", Amer. Chem. Soc., 21:12, pp. 435–441 (1998).
Silverstein et al., "Spectrometric identification of Organic Compounds", pp. 122–124, J. Wiley & Sons, New York (1981).
Sheehan et al., "Hyaluronic Acid: a Double–helical Structure in the Presence of Potassium at Low pH and Found also with the Cations Ammonium, Rubidium and Caseium", J. Mol Biol., 117, pp. 113–135 (1977).
De Tar et al., Reactions of Carbodiimides. I. The Mechanisms of the Reactionsof Acetic Acid with Dicyclohexylcarbodiimide, J. of the Am. Chem. Society, 88: 5, pp. 1013–1019 (1966).

* cited by examiner

*Primary Examiner*—Raymond Henley, III
(74) *Attorney, Agent, or Firm*—Isabella A. S. Blundell (57) ABSTRACT

A water insoluble, biocompatible gel is prepared by reacting carboxymethylcellulose and a carbodiimide, wherein the reaction is conducted in an aqueous medium containing a water miscible organic solvent, such as a lower alkanol, an alkyl pyrrolidone, DMSO or acetone. The present method permits the reaction to contain higher concentrations of carboxymethycellylose and less carbodiimide than conventional methods.

23 Claims, 2 Drawing Sheets

WATER INSOLUBLE DERIVATIVES OF POLYANIONIC POLYSACCHARIDES

BACKGROUND OF THE INVENTION

The present invention relates to biocompatible films and gels formed from chemically modified polyanionic polysaccharides. In particular, the present invention relates to biocompatible, polymeric gels which are prepared by synthesizing the polymer in a mixed solvent system containing water and a water miscible solvent such as a lower alkanol, an alkyl pyrrolidones, DMSO or acetone.

Polyanionic polysaccharides are polysaccharides containing more than one negatively charged group, e.g., carboxyl groups at pH values above about 4.0. One such polyanionic polysaccharide, hyaluronic acid ("HA"), is a naturally occurring mucopolysaccharide found, for example, in synovial fluid, in vitreous humor, in blood vessel walls and the umbilical cord, and in other connective tissues The polysaccharide consists of alternating N-acetyl-D-glucosamine and D-glucuronic acid residues joined by alternating β 1-3 glucuronidic and β 1-4 glucosaminidic bonds, so that the repeating unit is -(1→4)- β-D-GlcA-(1→3)-β-D- GlcNAc-. In water, hyaluronic acid dissolves to form a highly viscous fluid. The molecular weight of hyaluronic acid isolated from natural sources generally falls within the range of $5 \times 10^4$ up to $1 \times 10^7$ daltons.

As used herein the term "HA" means hyaluronic acid, and any of its hyaluronate salts, including, for example, sodium hyaluronate (the sodium salt), potassium hyaluronate, agnesium hyaluronate, and calcium hyaluronate.

HA, in chemically modified ("derivatized") form, is useful as a surgical aid, to prevent adhesions or accretions of body tissues during the post-operation period. The derivatized HA gel or film is injected or inserted into the locus between the tissues that are to be kept separate to inhibit their mutual adhesion. To be effective the gel must remain in place and prevent tissue contact for a long enough time so that when the gel finally disperses and the tissues do come into contact, they will no longer have a tendency to adhere.

Chemically modified HA can also be useful for controlled release drug delivery. Balazs et al., 1986, U.S. Pat. No. 4,582,865, states that "cross-linked gels of HA can slow down the release of a low molecular weight substance dispersed therein but not covalently attached to the gel macromolecular matrix." R. V. Sparer et al., 1983, Chapter 6, pages 107–119, in T. J. Roseman et al., *Controlled Release Delivery Systems*, Marcel Dekker, Inc., New York, describes sustained release of chloramphenicol covalently attached to hyaluronic acid via ester linkage, either directly or in an ester complex including an alanine bridge as an intermediate linking group.

I. Danishefsky et al., 1971, Carbohydrate Res., Vol. 16, pages 199–205, describes modifying a mucopolysaccharide by converting the carboxyl groups of the mucopolysaccharide into substituted amides by reacting the mucopolysaccharide with an amino acid ester in the presence of 1-ethyl-3-(3-dimethylaminopropyl) carbodiimide hydrochloride ("EDC") in aqueous solution. They reacted glycine methyl ester with a variety of polysaccharides, including HA. The resulting products are water soluble; that is, they rapidly disperse in water or in an aqueous environment such as is encountered between body tissues.

Proposals for rendering HA compositions less water soluble include cross-linking the HA. R. V. Sparer et al., 1983, Chapter 6, pages 107–119, in T. J. Roseman et al., *Controlled Release Delivery Systems*, Marcel Dekker, Inc., New York, describe modifying HA by attaching cysteine residues to the HA via amide bonds and then cross-linking the cysteine-modified HA by forming disulfide bonds between the attached cysteine residues. The cysteine-modified HA was itself water soluble and became water insoluble only upon cross-linking by oxidation to the disulfide form.

De Belder et al., PCT Publication No. WO 86/00912, describe a slowly-degradable gel, for preventing tissue adhesions following surgery, prepared by cross-linking a carboxyl-containing polysaccharide with a bi- or polyfunctional epoxide. Other reactive bi- or polyfunctional reagents that have been proposed for preparing cross-linked gels of HA having reduced water solubility include: 1,2,3,4-diepoxybutane in alkaline medium at 50.degree. C. (T. C. Laurent e al., 1964, Acta Chem. Scand., vol. 18, page 274); divinyl sulfone in alkaline 5 medium (E. A. Balasz et al., U.S. Pat. No. 4,582,865, (1986); and a variety of other reagents including formaldehyde, dimethylolurea, dimethylolethylene urea, ethylene oxide, a polyaziridine, and a polyisocyanate (E. A. Balasz et al., U.K. Patent Appl. No. 84 20 560 (1984). T. Malson et al., 1986, PCT Publication No. WO 86/00079, describe preparing cross-linked gels of HA for use as a vitreous humor substitute by reacting HA with a bi- or polyfunctional cross-linking reagent such as a di- or polyfunctional epoxide. T. Malson et al., 1986, EPO 0 193 510, describe preparing a shaped article by vacuum-drying or compressing a cross-linked HA gel.

SUMMARY OF THE INVENTION

The invention features an improved method for preparing a water insoluble gel by combining a polyanionic polysaccharide and an activating agent under conditions sufficient to form the gel. The reaction conditions of this invention include the use of an organic solvent which is selected from the group consisting of lower alkanols, alkyl pyrrolidones, DMSO and acetone. The organic solvents of this invention are miscible in water, and are present in the reaction medium in an amount of from about 5.0 % to about 80% by weight. A particularly preferred organic solvent is N-methylpyrrolidone, which is generally compatible with cardodiimide activating agents. N-methylpyrrolidone has a favorable biocompatibility profile in comparison to other organic solvents (rat $LD_{50}$=4 g/Kg), and it can be used to obtain a high concentration of modified polyanionic polysaccharides having a low viscosity.

The use of a water miscible organic solvent in the reaction medium as described herein permits the polyanioinic polysaccharide to be synthesized using substantially less activating agent and at a significantly increased concentration of reactants, as compared with a similar reaction conducted in water alone. The increase in concentration of reactants can amount to as much as six fold or more, and the reduction in activating agent, e.g. carbodiimide, can be on the order of one-third or more. As an example, the use of N-methylpyrrolidone permits the concentration of the reaction solution to be as high as 4.0% (40 g/L), with yields of up to 82%, as compared to concentrations of 0.6% (6 g/L) and 64% yields without the use of N-methylpyrrolidone. Since carbodiimides are relatively expensive reagents, a reduction in carbodiimide usage of this level can represent a significant cost savings. Typically, the derivatization reaction requires the use of approximately 6 molar equivalence of EDC per mole of carboxyl group, and includes a precipitation step involving large quantities of ethanol. The use of ethanol precipitation in a subsequent purification procedure, which involves the use of large quantities of ethanol, can be eliminated by following the procedure of this invention.

Preferred polyanionic polysaccharides for use in the present invention include hyaluronic acid, carboxymethyl cellulose ("CMC"), carboxymethyl amylose ("CMA"), carboxymethyl chitosan, chondroitin-6-sulfate, dermatin sulfate, heparin, and heparin sulfate; CMC and CMA are particularly preferred.

The preferred activating agent is a carbodiimide, e.g., 1-ethyl-3 -(3-dimethylaminopropyl)carbodiimide or 1-ethyl-3-(3 -dimethylaminopropyl)carbodiimide methiodide.

The activating agent can be added to the polyanionic polysaccharide, or the polyanionic polysaccharide may be combined with the activating agent. Combinations of different polyanionic polysaccharides can also be used.

The preferred pH for carrying out the reaction is 4.0 to 5.0. The preferred concentration for the polysaccharide is 0.2M–2.0M. The molar ratio of carboxyl groups of polysaccharide to activating agent is preferably less than about 1:1, and more preferably less than about 1:6.

The gel may be provided in the form of an adhesion prevention composition, e.g., in the form of a composition suitable for incorporation in a syringe or laproscopic instrument for use in minimal invasive surgical procedures. The gel may also include a pharmaceutically active substance dispersed throughout it; in such cases, the gel is useful as a drug delivery system. Suitable substances include growth factors, enzymes, drugs, biopolymers, and biologically compatible synthetic polymers. Alternatively, the gel can be used in applications where viscoelastic supplementation is desired, such as in the phacoemulsion surgery for the removal of cataracts in eye surgery to minimize the damage to endothelial cells.

A "biocompatible" substance, as that term is used herein, is one that has no medically unacceptable toxic or injurious effects on biological function. A polyanionic polysaccharide which is reacted with a suitable activating agent forms a gel having decreased water solubility without the use of and separately added bi- or polyfunctional cross-linking reagents.

A "water insoluble" gel of the invention, as that phrase and like terms are used herein, is one formed using a 1% aqueous solution of polyanionic polysaccharide, modified according to the invention, having the same dimensions and similarly allowed to stand without stirring in a beaker of 50 ml of distilled water at 20° C., remains structurally intact after 20 minutes, with the gel boundaries and edges still being present after 24 hours, although the gel is swollen.

A polyanionic polysaccharide is said to be "activated", as that term is used herein, when it is treated in an aqueous mixture in a manner that renders the carboxyl groups on the polyanionic polysaccharide vulnerable to nucleophilic attack; and an "activating agent" is a substance that, in an aqueous mixture including a polyanionic polysaccharide, causes the polyanionic polysaccharide to become so activated.

Because the gels are water insoluble, they can be thoroughly washed with water before use to remove unreacted substances. In addition, the gels can also be terminally stabilized by heat treatment without causing significant changes in the rheological properties of the gel prior to use.

The gels of the invention can also be prepared in colored form, by including a dye or stain in the reaction mixture. Such colored gels can be more easily seen when in place or during placement, making them easier to handle during surgical procedures than colorless ones.

The gels of the invention retain their strength even when hydrated. Because the gel adheres to biological tissues without the need for sutures, it is useful as postoperative adhesion prevention material. The gel can be applied to tissue even in the presence of bleeding.

Other features and advantages of the invention will be apparent from the following description of the preferred embodiments thereof, and from the claims.

DETAILED DESCRIPTION OF THE INVENTION

The gels of the invention are generally prepared as follows. CMC is dissolved in water to form an aqueous solution, followed by the addition of a solvent selected from the group consisting of a lower alkanol, an alkyl pyrrolidone, DMSO and acetone. The preferred lower alkanol is ethanol or isopropanol, and the preferred alkyl pyrrolidone is N-methyl-2-pyrrolidone. CMC can be obtained from a wide variety of commercial sources. Preferably, the concentration range of the CMC is from about 0.1% to about 8.0% weight/weight("w/w"). Higher concentrations can be achieved without significant increases in viscosity. The pH of the aqueous mixture is adjusted downward; then the dissolved CMC is activated by admixing a suitable activating agent, and allowed to stand until the desired gel has formed.

Increasing the concentration of the reagents generally has the effect of increasing the rate of the reaction. When water soluble carbodiimides are used in the reaction, however, there is a competing hydrolysis reaction with water which represents a major drawback. When the carbodiimide-polymer conjugate is formed, water can compete with the desired transformation, cleaving the conjugate into a urea by-product and the unmodified polymer. Decreasing the amount of water (by replacing it with an appropriate organic solvent) slows down the competing hydrolysis reaction allowing more product to be formed.

The aqueous CMC mixture should be acidic, preferably having a pH between pH 4.0 and pH 5.0, more preferably between pH 4.3 and pH 4.75. At lower pH values the preferred activating agent, EDC, is unstable, and at higher values the reaction rate is diminished. Preferably hydrochloric acid is added to adjust the pH, although other known acids can be used. The preferred polysaccharide concentration generally ranges from 0.2M to 2.0M. The preferred molar ratio of carboxyl groups of polysaccharide to activating agent is less than about 1:1, and more preferably less than about 1:6.

Once the pH of the aqueous CMC mixture has been adjusted, an activating agent is admixed. Preferred activating agents include carbodiimides, most preferably EDC (in some references this substance is termed 1-(3-dimethylaminopropyl)-3-ethyl-carbodiimide or "DEC") or ETC (1-ethyl-3-(3-dimethylaminopropyl)carbodiimide methiodide).

The mechanism for the reaction of carbodiimide with carboxylic acids is shown below:

NUC = amines, alcohols, phenols, carboxylates, water

The reaction proceeds through an O-acylisourea ("OIU") intermediate that can undergo nucleophile substitution with an added nucleophile (i.e., an amine), or undergo an O→N rearrangement to give the more stable N-acylurea ("NAU"). In the case of aqueous reactions, water hydrolyzes the OIU intermediate resulting in very low derivatization of carboxyl groups. Therefore, reactions of diimide with carboxyl groups in water requires a large excess of the diimide reagent.

This problem has been solved by diluting the water content with an organic solvent, preferably a polar aprotic solvent, thereby reducing the competing hydrolysis. Using this procedure, it is possible to formulate a 4.0% (40 g/L) solution of CMC in a 1:1 mixture of N-methylpyrrolidone:water. The decrease in water content as well as the high polymer concentration thus results in a three-fold decrease in the amount of carbodiimide needed to form the gel. It is thus surprising that a gel precipitate is formed in a matter of minutes following this procedure after the addition of the EDC to the reaction mixture.

The gel can be isolated using a polyethylene mesh screen and excess reagent and side-products removed by consecutive washing with water. This eliminates the need for large volumes of ethanol to isolate the modified material. The isolated gel can be formulated to a desired viscosity by high shear mixing with an appropriate buffer, packaged into syringes and terminally sterilized in an autoclave. The gels are quite robust, surviving the heat treatment with minimal Theological change.

If a colored product is desired, a solution of a dye or stain such as the blue dye "Brilliant Blue R", also known as "Coomassie™ Brilliant Blue R-250", distributed as "Serva Blue" by Serva, can be admixed to the reaction mixture at this point. The resulting product has a blue color that can provide a good contrast to the color of body tissues, making the gel easy to see while it is handled during surgery and once it is in place.

Once the reagents (and the stain or dye, if any) have been admixed, the reaction mixture can be simply allowed to stand for a time, or it can be continually or occasionally stirred or agitated.

Upon admixing of the reagents the pH rises, and can be maintained at the desired pH by addition of acid as the reaction proceeds. We have found, however, that gels with various desired physical properties can be obtained by simply allowing the pH to rise as the reaction proceeds.

The resulting gel can be harvested without the use of expensive and potentially harmful solvents, such as ethanol, isopropanol, acetone, and other solvents that can cause the polymer to pecipitate from an aqueous solution. This is accomplished by allowing the gel to precipitate from the reaction mixture, and collecting the gel by filtration. The harvested gel is washed with water, formulated to achieve the desired rheological properties, and then terminally heat sterilized without apparent change in the gel properties.

If desired, the gel can be washed prior to use by, for example, perfusion with water or 1M aqueous sodium chloride. Alternatively the reaction mixture can be dialyzed to remove residual reagents prior to casting it as a film. Washing to remove residual reagents or reagent-derived material such as substituted ureas is desirable if the gel is to be used for therapeutic applications. Gels colored blue with Brilliant Blue R as described above do not lose their coloration during such washing. The removal of reagents or reaction products can be monitored by high pressure liquid chromatography.

The invention is described in more detail in the following examples. These examples are provided by way of illustration only, and are not intended to limit the invention except as set forth in the appended claims. As one skilled in the art will appreciate, the gels of the invention can be made using protocols that are within the method of the invention yet are different in particulars from those described here.

EXAMPLE 1

In this example gels were prepared using EDC as an activating agent and leucine methyl ester 5 hydrochloride as a nucleophile.

Sodium hyaluronate (400 mg; 1.0 mmol of carboxyl groups) having a molecular weight between $1 \times 10^6$ and $2 \times 10^6$ was dissolved in 10 ml of distilled water. The pH of the aqueous solution was adjusted to pH 4.75 by the addition of 0.1N HCl. Then 314 mg of EDC (1.64 mmol) was added all at once followed by 190 mg (1.05 mmol) of L-leucine methyl ester hydrochloride. The pH of the reaction mixture then rose to 6.2 over two hours. The reaction mixture was kept at room temperature for five hours, after which time it had formed a thick insoluble gel. This gel could be washed with a 1M NaCl solution to remove residual reagents without loss of its physical properties.

EXAMPLE 2

In this example various EDC/leucine:HA ratios were used for comparison of gel formation and properties.

The procedure was as in Example 1, using sodium hyaluronate (400 mg; 1.0 mmol of carboxyl groups) in 15 ml of water. In separate experiments the following quantities of EDC and leucine methyl ester hydrochloride were then added: 153 mg EDC (0.8 mmol)/182 mg leucine methyl ester hydrochloride (1.0 mmol); 76 mg EDC (0.4 mmol)/90 mg leucine methyl ester hydrochloride (0.5 mmol); and 38 mg EDC (0.2 mmol)/45 mg leucine methyl ester hydrochloride (0.25 mmol). Strong gels were obtained as in Example 1 for the highest ratio of EDC and leucine methyl ester hydrochloride. At the lowest ratio of reactants (0.2 mmol/0.25 mmol to 1.0 mmol HA carboxyl groups) a weak gel was obtained, which collapsed to a fluid after two weeks.

EXAMPLE 3

In this example the HA concentration was reduced by one-half for comparison of resulting gel properties.

The procedure was as in Example 1 except the HA (400 mg; 1.0 mmol of carboxyl groups) was dissolved in 30 ml of water rather than 15 ml (1⅓% w/w HA). A gel was formed, although it was weaker than that obtained in Example 1.

EXAMPLE 4

In this example films were prepared using EDC as an activating agent and leucine methyl ester hydrochloride as a nucleophile.

Sodium hyaluronate (400 mg; 1.0 mmol of carboxyl groups) was dissolved in 40 ml of distilled water. The pH of the solution was adjusted to pH 4.75 by addition of 0. IN HCl. Then EDC (314 mg; 1.64 mmol) was added in a single portion, followed by 190 mg (1.05 mmol) of L-leucine methyl ester hydrochloride. The pH of the reaction mixture rose to 6.2 during two hours, after which time the solution was poured into a petri dish of area 6360 mm.sup.2, and allowed to dry to a film over a two day period. Films produced in this manner were strong and insoluble in water and 1M aqueous NaCl. The films could be washed with water or aqueous NaCl as in Example to remove residual reagents without loss of their physical properties. Infrared spectroscopic analysis of such films showed no carbodiimide absorption at about 2130 cm.sup.-i and displayed absorptions at about $1740$ $cm^{-1}$, $1700$ $cm^{-1}$, $1650^{-1}$, and $1550^{-1}$.

EXAMPLE 5

In this example various HA concentrations were used in making films for comparison of resulting film properties.

The procedure described in Example 4 was repeated, using three different initial HA concentrations made by dissolving the HA (400 mg; 1.0 mmol of carboxyl groups) in 30 ml, 40 ml, or 100 ml of distilled water. Films produced using each of these initial concentrations of HA were strong and insoluble in water and 1 M aqueous NaCl, showing that a range of concentrations of HA can be used. Each of these films could be washed with water or aqueous NaCl without loss of its physical properties.

EXAMPLE 6

This example illustrates the effect of dialyzing the reaction mixture prior to casting to form a film, as compared with washing the film after forming it.

Sodium hyaluronate (400 mg in 40 ml of water), EDC (314 mg; 1.64 mmol) and L-leucine methyl ester hydrochloride (190 mg; 1.05 mmol) were allowed to react as in Example 4. Upon completion of the reaction (2 hours), the reaction mixture was dialyzed against water, through 12,000 NMW cutoff dialysis tubing in order to remove residual reagents. The dialyzed mixture was then cast as a film as in Example 4. The film so obtained was strong and insoluble in water or 1M aqueous NaCl.

EXAMPLE 7

In this example films were formed by drying more thickly poured reaction mixtures, to compare the properties of films produced from drying mixtures at differing surface area/volume.

A reaction mixture obtained as in Example 4 (40 ml reaction volume) was cast into a small petri dish (area 3330 mm ). The film so obtained was insoluble in 1M aqueous NaCl and in water (100° C.; 1 hour).

EXAMPLE 8

In this example films were prepared using other amino acid esters and HA activated with EDC.

A solution of HA (400 mg in 40 ml of $H_2O$) was brought to pH 4.7 using 0.1N HCl. Then EDC (314 mg; 1.6 mmol) was added all at once followed by 1 mmol of the amino acid derivative. The reaction mixture was poured into a petri dish and allowed to dry. Insoluble films were obtained from L-valine methyl ester hydrochloride, L-isoleucine methyl ester hydrochloride, L-proline methyl ester hydrochloride, and L-phenylalanine methyl ester hydrochloride.

EXAMPLE 9

In this example films were prepared using a simple primary amine (aniline) as a nucleophile.

A solution of HA (400 mg in 40 ml of $H_2O$) was brought to pH 4.7 using 0.1N HCl. Then EDC (314 mg; 1.6 mmol) was added all at once followed by 1 mmol of aniline. The reaction mixture was poured into a petri dish and allowed to dry, and insoluble films were obtained.

EXAMPLE 10

In this example films were prepared using other esters of leucine.

A solution of HA (400 mg in 40 ml of $H_2O$) was brought to pH 4.7 using 0.1N HCl. Then EDC (314 mg; 1.6 mmol) was added all at once followed by 1 mmol of the leucine ester. The reaction mixture was poured into a petri dish and allowed to dry. Insoluble films were obtained from both L-leucine ethyl ester hydrochloride and L-leucine t-butyl ester hydrochloride.

EXAMPLE 11

In this example gels were prepared using other amino acid methyl esters.

A solution of HA (400 mg in 15 ml of $H_2O$) was brought to pH 4.7 and EDC (314 mg; 1.6 mmol) was added, followed by the amino acid derivative (1 mmol). The reaction mixture formed a thick gel within from 5 to 24 hours. Water insoluble gels were obtained using L-valine methyl ester hydrochloride, L-isoleucine methyl ester hydrochloride, L-arginine methyl ester hydrochloride, L-proline methyl ester hydrochloride, and L-histidine methyl ester hydrochloride.

EXAMPLE 12

In this example films were prepared using an amino acid amide (leucinamide) as a nucleophile.

A solution of HA (400 mg in 40 ml of $H_2O$) was brought to pH 4.7 using 0.1N HCl. Then EDC (314 mg; 1.6 mmol)

was added all at once followed by 1 mmol of L-leucinamide hydrochloride. The reaction mixture was poured into a petri dish and allowed to dry and insoluble films were obtained.

EXAMPLE 13

In this example gels were prepared using leucine ethyl ester hydrochloride.

A solution of HA (400 mg in 15 ml of $H_2O$) was brought to pH 4.7 and EDC (314 mg;

1.6 mmol) was added, followed by leucine ethyl ester hydrochloride (1.0 mmol). The mixture formed a thick, water insoluble gel within from 5 to 24 hours.

EXAMPLE 14

In this example films and gels were prepared using ETC as the HA activating agent.

Sodium hyaluronate (400 mg, 1.0 mmol of carboxyl groups) having a molecular weight in the range between 1. times $10.^6$ and 2. times $10.^6$ daltons was dissolved in water (10 ml and 30 ml). The pH of each aqueous solution was adjusted to pH 4.75 by addition of 0.1N HCl. Then 475 mg of ETC (1.6 mmol) was added all at once, followed by 190 mg (1.05 mmol) of L-leucine methyl ester hydrochloride. The pH of this reaction mixture rose to pH 6.2 over the next 2 hours. The reaction mixture containing 10 ml of water formed an insoluble gel. The reaction mixture containing 30 ml of water gave an insoluble film after drying.

EXAMPLE 15

This example illustrates the preparation of a colored film.

A solution of HA (400 mg in 30 ml of $H_2O$) was brought to pH 4.75 as in Example 13 and then ETC (475 mg; 1.6 mmol) and leucine methyl ester hydrochloride (190 mg; 1.05 mmol) were added. A dilute solution of "Serva Blue" (5 mg/ml) dye in $H_2O$ (0.5 ml) was then added to the reaction mixture. The resulting mixture was poured into a petri dish and a water insoluble blue film was obtained after 16 hours. The blue color was retained by the film when the film was washed with 1M NaCl and then with $H_2O$.

EXAMPLE 16

This example illustrates the tissue biocompatibility of a film of chemically modified HA.

Four strips of films prepared according to the procedure described in Example 4, and two USP negative control strips were surgically implanted into the paravertebral muscle of White New Zealand rabbits (two per test). The test sites were evaluated either macroscopically after 72 hours or with complete histopathology after 7 days. In accordance with the USP XXI, p. 1237, the test material met the requirements of the USP Implantation Test for the Evaluation of Plastic Materials.

EXAMPLE 17

This example illustrates the preparation of lysine-modified HA.

A 0.4%(w/w) solution of HA in water was prepared. The pH of this solution was adjusted to between 4.3 and 4.75 by addition of acid. To each 100 ml of this solution was added 0.76 g of EDC with stirring until the EDC had completely dissolved. To each 100 ml of the HA/EDC solution was added 0.20 g of lysine methyl ester (LME) with stirring until the LME had completely dissolved. The addition of HA, EDC, and LME was conducted at room temperature; once the final HA/EDC/LME solution had been formed, it was stored at 4° C. until needed.

The LME-modified HA material can be processed into various shapes, sizes, and consistencies depending on the end application. If a thin sheet of the material is desired, the mixture can be poured onto a flat surface. This material can then be turned into a solid by allowing the water to evaporate under ambient or elevated temperatures. An alternative method of producing sheets of the material is to subject it to freeze drying. The pore size of the final product can be controlled by adjusting the initial freezing temperature. Curved surfaces and other shapes can be produced in a similar manner by initially casting the gel onto a negative image surface and then processing as described. The dried sheet can be processed further, if desired, by pressing to a defined thickness in a Carver laboratory press. This is particularly useful for applications requiring placing a thin film between anatomical structures where space is limited.

Mechanical testing of the freeze-dried material, rehydrated in normal saline, resulted in force-to-break values of 170–900 g/cm$^2$. The elongation to break values for this material were between 33% and 62%.

EXAMPLE 18

This example illustrates the preparation of CMC-modified HA.

HA (0.4% w/w, 0.01M) and Aqualon-type CMC having a molecular weight of 250,000 and a degree of substitution in the range 0.65 to 0.90 (0.19% w/w, 0.01M) were mixed together in aqueous solution at room temperature. The pH of the mixture was adjusted to and maintained at pH 4.7–4.8 by addition of 1M HCl. To each 100 ml of this solution was added 0.67 g (0.04M) EDC. During reaction with EDC, the pH of the solution was maintained at pH 4.7–4.8 by addition of 0.1M HCl and the reaction allowed to proceed for 1 hour, during which time a precipitate formed. The unreacted EDC was removed from the precipitate by dialysis against acidified water (pH 4.0) for 24 hours with 2 dialysate changes at 3 and 19 hours. The HA/CMC slurry was then cast into flat molds and air dried for 24 hours at room temperature.

HA/CMC membranes were shown to reduce the incidence of postoperative adhesion formation in experimental animal models. In experiments using the rat cecal abrasion model, HA/CMC membranes were placed around surgically abraded rat ceca; previous studies had demonstrated that adhesions readily formed on the ceca of rats which had been abraded in controlled fashion. Cecal adhesions in animal groups that received either HA/CMC membranes or ORC membranes (Interceed TC7 membranes marketed by Johnson & Johnson for adhesion prevention) were compared to adhesion controls in animals whose ceca were abraded but did not receive any membrane. The results of these experiments showed that the HA/CMC membranes consistently reduced adhesion formation compared to control animals and to animals that received the Interceed TC7 film.

EXAMPLE 19

This example illustrates the preparation of EDC-activated HA.

HA (1.0×10$^6$ daltons) was dissolved in water to make a 0.8% w/v solution by stirring overnight at 25° C. The pH of the reaction mixture was adjusted to pH 4.75 with 0.1N HCl. EDC (4:1 molar ratio of EDC to HA, 1.53% w/v final concentration) was added to this solution with continuous stirring and was maintained at a constant pH (4.7–5.1) for one hour by adding additional 0.1N HCl. Removal of the unreacted EDC and other low molecular weight impurities was performed by either molecular weight sizing, dialysis, or diafiltration using standard methods. A water-insoluble, clear gel was obtained after this process.

EXAMPLE 20

This example illustrates the effect of fractional precipitation of EDC-activated HA with a water soluble solvent.

The procedure described in Example 19 was repeated with the exception that unreacted EDC and other low molecular weight impurities were removed by fractional precipitation using a suitable water-soluble solvent (e.g., C1–C3 alchohols, acetone). Under these conditions, water insoluble fibers were produced.

EXAMPLE 21

This example illustrates the preparation of EDC-activated CMC.

CMC ($250 \times 10^3$ daltons) was dissolved in water to make a 0.8% w/v solution by stirring at room ambient temperature (22° C.–25° C.) overnight. The pH of the reaction mixture was adjusted to pH 4.75 with 0.1N HCl. EDC (4:1 molar ratio of EDC to CMC, 1.53% w/v final concentration) was added to this solution with constant stirring and the pH was maintained between 4.70 and 5.10 for one hour by adding additional 0.1N HCl. Removal of the unreacted EDC and other low molecular weight impurities is performed by using either seizing chromatography, dialysis, diafiltration, or fractional precipitation of the CMC with a suitable water-soluble solvent (e.g., $C_1$–$C_3$ alcohols, acetone). Water insoluble fibers, approximately 300–800 $\mu$m long and 10–20 $\mu$m wide, are produced from these reaction conditions.

EXAMPLE 22

This example illustrates the preparation of a blend of EDC-activated HA with EDC-activated CMC.

EDC-activated HA and CMC were prepared separately as described in Examples 19 and 21, but each reaction product was not purified prior to blending. 300 ml of the activated HA and 300 ml of the activated CMC were placed in a 1000 ml beaker, and blended with a Turrax brand blender at 6000 rpm for 10 minutes at 25° C. The resulting mixture was purified by dialysis against pH 4.0 water for 24 hours at a 20:1 ratio with 3 dialystate exchanges. After dialysis the mixture was poured into a flat mold and air dried to a thin water insoluble film. The quality of fibers in the mixture can be controlled by varying the relative amount of activated CMC and activated HA that are blended together.

EXAMPLE 23

This example illustrates the preparation of an EDC-activated CMC composition in N-ethyl-2-pyrrolidone.

CMC was dissolved in water to make a 08.0% w/v solution. 150 ml of this solution was mixed with 150 ml of N-methyl-2-pyrrolidone ("NMP"), followed by stirring at ambient temperature for 20 minutes. 6.0 ml of 6N HCl was added to this solution, followed by 14.75 grams of EDC in 15.0 ml of D.I. water. The reaction immediately formed gel particles upon the addition of the EDC solution.

The slurry was allowed to stand at room temperature for 10 minutes, at which point the precipitate was collected on a mesh filter and washed three consecutive times with 1 L each of D.I. water. The resulting gel particles were dispersed into buffer or saline solutions, and homogenized to a consistent viscosity with a high shear mixer (IKA-Labortechnik ultra Torax, model T25).

The gel was then filled into 20 ml syringes (B-D Hypak) and autoclaved in a custom-built syringe holder for 15 minutes at 121° C. Alternatively, the gel particles can also be dehydrated with ethanol to give a white, flocculent powder that can be stored in the dry state and formulated at a later time. The yield is approximately 82%.

EXAMPLE 24

This example illustrates the preparation of an EMC-activated CMC composition in acetone.

The procedure described in Example 23 was repeated with the exception that the N-methyl-2-pyrrolidone solvent was replaced with acetone. Upon addition of the EDC, the reaction formed gel particles as in Example 23, and the particles were easily collected by filtration. The resulting product was either washed with water and used directly, or precipitated in ethanol and collected as a fine white powder.

EXAMPLE 25

This example illustrates the preparation of an EMC-activated CMC composition in ethanol.

The procedure described in Example 23 was repeated with the exception that the N-methyl-2-pyrrolidone solvent was replaced with acetone. The results were substantially the same as described in Example 24.

EXAMPLE 26

This example illustrates the preparation of an EMC-activated CMC composition in isopropanol.

The procedure described in Example 23 was repeated with the exception that the N-methyl-2-pyrrolidone solvent was replaced with isopropanol. The results were substantially the same as described in Example 24.

Table 1 below shows the effect of reaction time on the viscosity of gels prepared from the corresponding reaction products. The product gel viscosity increases with increasing reaction time over 20 minutes. After 20 minutes the reaction product viscosities rapidly decrease.

TABLE 1

| Reaction Time (min) | Phase Angle (°) | G* (Pa) | Yield Stress (Pa) | Viscosity (cP) |
|---|---|---|---|---|
| 5 | 21 | 199 | 2 | 17853 |
| 20 | 27 | 47 | 2 | 24479 |
| 40 | 29 | 35 | 2 | 7256 |
| 60 | 30 | 25 | 2 | 4838 |

Table 2 below shows the reagent stoichiometries and reaction parameters for a CMC/NAU reaction performed in the presence or absence of the NMP solvent system. The gels were prepared from the 10 min reaction of EDC with CMC in the NMP solvent were terminally sterilized at 121° C. for 20 min. The reactions were run side-by-side with the isolation of the NMP solvent gel as described above. The non-NMP solvent reaction product did not precipitate to the extent that the NMP reaction did, making isolation of the gel particles more difficult.

TABLE 2

| Parameter | NMP Reaction | Non-NMP Reaction |
|---|---|---|
| [CMC] (%) | 4.0 | 4.0 |
| EDC:CMC | 1.5:1 | 1.5:1 |
| Rxn pH | 4.25 | 3.81 |
| Rxn T° C. | 29 | 29 |
| Reaction Time (min) | 10 | 10 |

Table 3 below shows the chemical composition for NMP and non-NMP reactions. The NMP reaction yields a gel product with a 1.7 fold increase in modification and a 1.3 fold increase in yield.

TABLE 3

| Component | NMP Reaction | Non-NMP Reaction |
|---|---|---|
| % CMC | 89 | 81 |
| % Urea | 5.9 | 3.5 |
| % LOD | 11.4 | 8.02 |
| % Yield | 82 | 64 |

Figure 1:
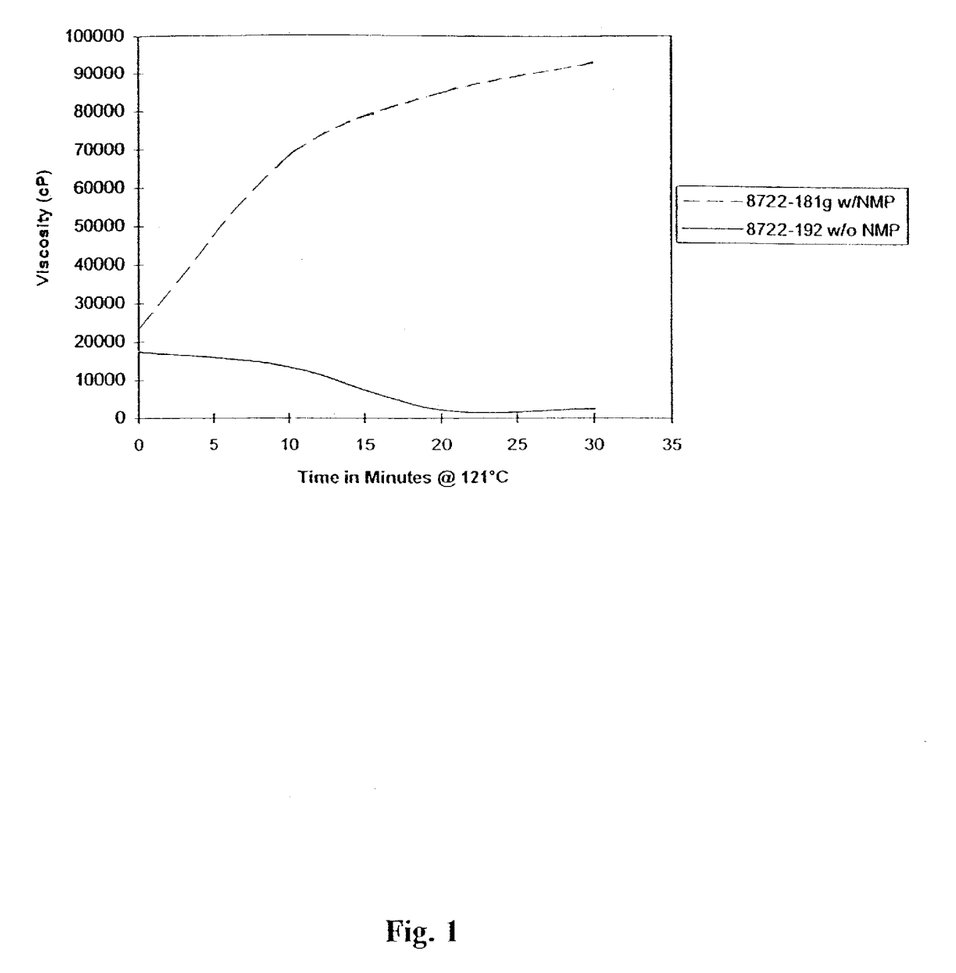
FIG. 1 is a graph showing the change in viscosity during heat treatment of N-acylurea modified CMC gels, both with and without N-methyl-2-pyrrolidone.
Figure 2:
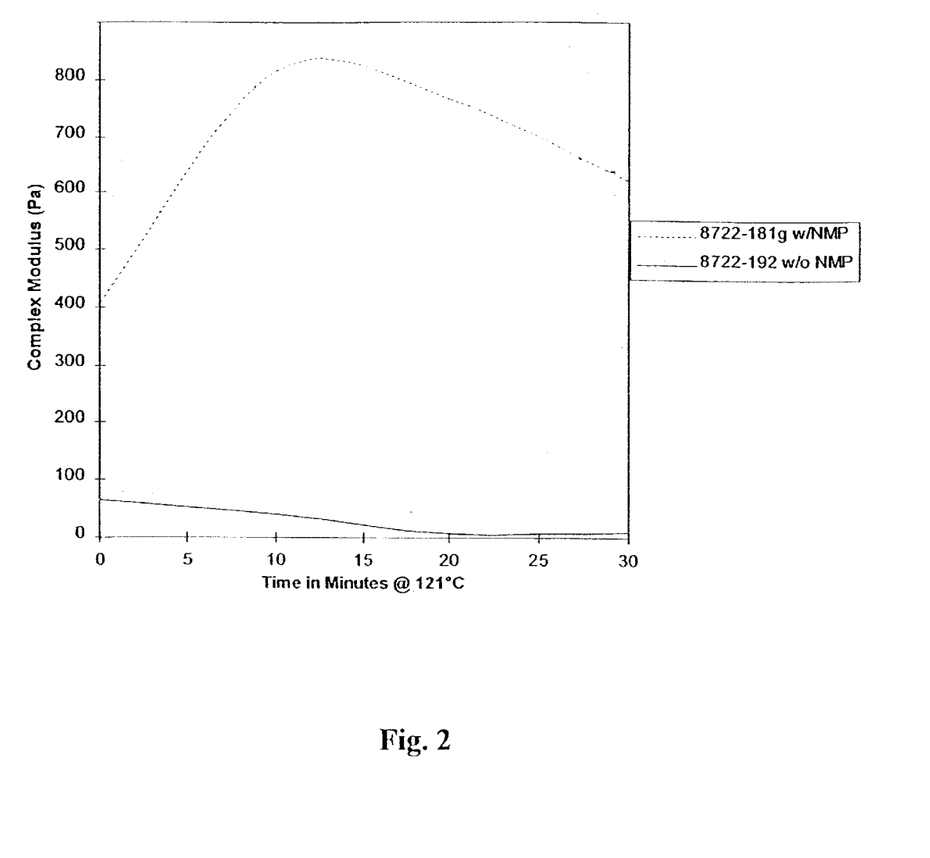
FIG. 2 is a graph showing the change in the complex modulus during heat treatment for N-acylurea modified CMC gels, both with and without N-methyl-2-pyrrolidone.

FIGS. 1 and 2 compare the heat stability profiles for viscosity and complex modulus (an indicator of gel strength) for CMC/NAU gels prepared with and without the NMP solvent system (50/50 mixture of NMP and water). The gels made with the NMP system show no significant change in complex modulus and a gradual increase in viscosity with heating at 121° C. The samples prepared from the non-NMP reaction powder did not form robust gels that dissolved very quickly upon heating.

Autoclaved CMC/NAU NMP gels were then tested for the ability to reduce post surgical adhesions in a rat cecal abrasion model. The results in Table 4 show that the CMC/NAU NMP gels significantly reduce the mean incidence of adhesions and increase the number of adhesion free animals when compared to the untreated control.

TABLE 4

| Group | N | % w/adh ≧ 2 | Avg. Inc. ± SEM | % w/ no adh |
|---|---|---|---|---|
| Control | 10 | 60 | 1.5 ± 0.5 | 40 |
| CMC/NAU NMP Gel | 10 | 20 | 0.4 ± 0.3 | 80 |

The gels of this invention can be used as surgical aids, to prevent adhesions or accretions of body tissues during a post-operation or healing periods, following procedures known in the surgical arts, as described, for example, in DeBelder et al., PCT Publication No. WO 86/00912. During surgery one or more portions of the gel, as appropriate, can be inserted or injected into the locus between or among the tissues that are to be kept separate. A suitable applicator is a laproscopic instrument which can be used in minimally invasive surgical applications. The gel is biocompatible and biodegradable, so that it remains in the body for only the time it takes to prevent the formation of the adhesions, and then it is reabsorbed.

The gels of the invention can also be used for sustained release drug delivery. The drug to be delivered can be covalently bonded to the gel or film, as described, for example, in R. V. Sparer et al., 1983, Chapter 6, pages 107–119, in T. J. Roseman et al., Controlled Release Delivery Systems, Marcel Dekker, Inc., New York; and the gel can then be implanted or injected at the locus where delivery is desired. The gels of this invention are also useful for viscoelastic supplementation, such as in phacoemulsion surgery for the removal of cataracts in order to minimize the damage to endothelial cells in eye surgery.

OTHER EMBODIMENTS

Other embodiments are within the scope of the following claims.

What is claimed is:

1. A method for preparing a water insoluble biocompatible gel comprising reacting a polyanionic polysaccharide with an activating agent in an aqueous solution containing a water miscible organic solvent selected from the group consisting of a lower alkanol and a polar aprotic solvent.

2. The method of claim 1 wherein the polar aprotic solvent is selected from the group consisting of an alkyl pyrrolidones, DMSO and acetone.

3. The method of claim 1 wherein said polyanionic polysaccharide is chosen from the group consisting of hyaluronic acid, carboxymethyl cellulose, carboxymethyl amylose, carboxymethyl chitosan, chondroitin-6-sulfate, dermatin sulfate, heparin, and heparin sulfate.

4. The method of claim 3 wherein said polyanionic polysaccharide is hyaluronic acid.

5. The method of claim 3 wherein said polyanionic polysaccharide is carboxymethyl cellulose.

6. The method of claim 1 wherein said activating agent comprises a carbodiimide.

7. The method of claim 6 wherein said carbodiimide comprises 1-ethyl-3-(3-dimethylaminopropyl) carbodiimide, or 1-ethyl-3-(3-dimethylaminopropyl) carbodiimide methiodide.

8. The method of claim 1 wherein the solvent is a lower alkanol.

9. The method of claim 8 wherein the solvent is ethanol or isopropanol.

10. The method of claim 2 wherein the solvent is an alkyl pyrrolidone.

11. The method of claim 10 wherein the solvent is N-methyl-2-pyrrolidone.

12. The method of claim 2 wherein the solvent is DMSO.

13. The method of claim 2 wherein the solvent is acetone.

14. The method of claim 1 wherein the concentration of solvent in the solution is in the range of from about 5% to about 80% by weight.

15. The method of claim 1 wherein polyanionic polysaccharide is present in a concentration range of 0.2M to 2.0M.

16. The method of claim 1 wherein said method is carried out at a pH of 4.0 to 5.0.

17. The method of claim 1 wherein the molar ratio of carboxyl groups of said polyanionic polysaccharide to said activating agent is less than about 1:1.

18. The method of claim 17 wherein the molar ratio of carboxyl groups of said polyanionic polysaccharide to said activating agent is less than about 1:4.

19. A water insoluble biocompatible gel prepared according to the method of claims 4 or 5.

20. The gel of claim 19 further comprising a pharmaceutically active substance dispersed within said gel.

21. The gel of claim 20 wherein said pharmaceutically active substance is chosen from the group consisting of growth factors, enzymes, drugs, biopolymers, and biologically compatible synthetic polymers.

22. A method of preventing post-operative adhesions comprising inserting, into the locus between tissues to be separated during the healing process following surgery, the water insoluble, biocompatible gel of claim 19.

23. The method of claim 22 wherein the gel is inserted into the locus between tissues using a laparoscopic instrument during a minimally invasive surgical procedure.

* * * * *